United States Patent [19]
Black et al.

[11] Patent Number: 5,651,397
[45] Date of Patent: Jul. 29, 1997

[54] DUAL CHAMBER DISPENSING CARTRIDGE REFILLING DEVICE

[75] Inventors: Kevin L. Black, Redmond, Wash.; Frederick J. Turk, St. Paul; Bruce R. Broyles, Oakdale, both of Minn.

[73] Assignee: Minnesota Mining and Manufacturing Company, St. Paul, Minn.

[21] Appl. No.: 558,844

[22] Filed: Nov. 15, 1995

[51] Int. Cl.$^6$ ............... B65B 1/04; B65B 3/04; B65B 31/00; B67C 3/00
[52] U.S. Cl. ............... 141/18; 141/25; 141/27; 141/237; 141/247; 141/346; 285/124.1
[58] Field of Search ............... 141/9, 18, 25, 141/27, 99, 234, 237, 242, 247, 383, 384, 346; 285/131, 137.1; 92/151

[56] References Cited

U.S. PATENT DOCUMENTS

| | | | |
|---|---|---|---|
| 4,199,081 | 4/1980 | Mason | 222/43 |
| 4,274,453 | 6/1981 | Lee | 141/1 |
| 4,421,146 | 12/1983 | Bond et al. | 141/349 |
| 4,434,820 | 3/1984 | Glass | 141/2 |
| 4,538,920 | 9/1985 | Drake | 366/177 |
| 4,551,135 | 11/1985 | Gorman et al. | 604/82 |
| 4,750,532 | 6/1988 | Grothoff | 141/27 |
| 4,974,756 | 12/1990 | Pearson et al. | 222/562 |
| 5,020,693 | 6/1991 | Ernst et al. | 222/137 |
| 5,064,098 | 11/1991 | Hutter, III et al. | 222/137 |
| 5,080,493 | 1/1992 | McKown et al. | 366/177 |
| 5,092,492 | 3/1992 | Centea | 222/137 |
| 5,137,181 | 8/1992 | Keller | 222/134 |
| 5,236,108 | 8/1993 | House | 222/541 |
| 5,289,949 | 3/1994 | Gentile | 222/137 |
| 5,304,165 | 4/1994 | Haber et al. | 604/411 |
| 5,335,827 | 8/1994 | Gentile | 222/137 |

FOREIGN PATENT DOCUMENTS

| | | |
|---|---|---|
| 0539074A1 | 4/1993 | European Pat. Off. . |
| WO95/22941 | 8/1995 | WIPO . |

*Primary Examiner*—Henry J. Recla
*Assistant Examiner*—Timothy L. Maust
*Attorney, Agent, or Firm*—Gary L. Griswold; Walter N. Kirn; James D. Christoff

[57] ABSTRACT

A device for consolidating compositions contained in partially filled dual chamber dispensing cartridges includes a body having a pair of passages, and first and second couplers for connecting the body to first and second dual chamber dispensing cartridges. Once the device is connected to two cartridges, an applicator is connected to one of the cartridges and is used to expel any remaining compositions in such cartridge to chambers of the other cartridge. The contents of several partially empty cartridges can be consolidated in this manner so that a subsequent dispensing operation need not be interrupted to replace cartridges.

15 Claims, 9 Drawing Sheets

DUAL CHAMBER DISPENSING CARTRIDGE REFILLING DEVICE

BACKGROUND OF THE INVENTION

1. Field of the Invention

This invention relates to a device for refilling or partially refilling a dual chamber dispensing cartridge used to contain and dispense two components of plural component material such as epoxies or dental impressioning material.

2. Description of the Related Art

Dual chamber dispensing systems are widely used for dispensing material that is made of two components or compositions. Examples of such material in the fields of construction and manufacturing include adhesives, coatings, sealants and potting compounds, while examples of such material in the medical field include dental impressioning material. Dual chamber dispensing systems often include a replaceable cartridge that has separate, side-by-side barrels with chambers that each hold one component of the material to be dispensed. Examples of dual chamber dispensing cartridges are described in U.S. Pat. Nos. 4,538,920 and 5,236,108.

Many dual chamber dispensing systems also include an applicator having a receptacle for removably receiving a dual chamber cartridge. Some applicators are adapted to be held by the hand during use, and include a pair of handles that, when squeezed together, simultaneously advance a pair of side-by-side plungers by means of a ratchet mechanism. As the plungers advance, the ends of the plungers contact respective pistons located in the chambers of the dispensing cartridge and move the pistons in a forwardly direction toward the front of the cartridge. As the pistons advance, the pistons expel the two components contained in both chambers simultaneously through respective outlets that are located near the front of the cartridge. Examples of hand-held applicators for dual chamber dispensing cartridges are described in EP Publication No. 0 539 074 A1, U.S. Pat. No. 5,137,181 and pending U.S. patent application Ser. No. 08/547,370, entitled "HAND-HELD APPLICATOR WITH FORCE LIMITING CLUTCH".

In some instances, and particularly in construction, manufacturing and industrial applications, electric or pneumatic operated applicators are used to dispense compositions from dual chamber dispensing cartridges. Electric applicators may be battery powered for convenient, hand-held manipulation, or instead may be powered by line current, a particular advantage when relatively large quantities of the components are to be dispensed. In areas where compressed air is readily available, air powered applicators may be preferred. Examples of powered dispensing applicators are described in U.S. Pat. Nos. 5,020,693, 5,064,098 and 5,080,493.

Dual chamber dispensing systems also often include a static mixer for mixing the components that are expelled from the cartridge. The static mixer includes an exit conduit that is detachably coupled to the front end of the cartridge and that communicates with the two spaced apart front outlets of the cartridge. A static mixing element is located within the exit conduit and includes a series of helical shaped mixing sections. When the plungers of the applicator are advanced to expel components from the cartridge, the components pass through the exit conduit where they are thoroughly mixed together by the successive mixing sections and then discharged through a front opening of the exit conduit, optionally directly to an application site. Examples of static mixers are described in U.S. Pat. No. 4,538,920 and PCT publication no. WO 95/22941.

In the dental arena, dual chamber dispensing systems are used to dispense two component impressioning material so that a model of the patient's teeth and gingiva can be obtained. In some procedures, the mixed impressioning material is dispensed into a dental impression tray that is then placed in the patient's oral cavity over selected teeth and gingiva. Once the material hardens, the tray is removed from the mouth and a model of the patient's teeth and gingiva is made by pouring a hardenable plaster of Paris solution, a resin or other molding material into the negative image formed in the impressioning material. After the molding material has hardened, the impressioning material is removed from the molding material in order to obtain a positive model of the patient's teeth and gingiva.

Dispensing cartridges are typically sold containing a larger quantity of impressioning material components than is expected to be needed to fill a typical tray. One reason that the cartridges contain a larger quantity of components than expected to be needed is due to the fact that the trays are available in a wide range of shapes and sizes, so that a particular tray can be selected to match the shape and size of the patient's dental arch that is encountered in practice. Manufacturers typically supply cartridges with a sufficient quantity of components to fill the largest expected tray. Consequently, unless the selected tray is unusually large, a quantity of the components often remains in the cartridge after the tray has been filled.

A dental impressioning dispensing cartridge that has been only partially emptied after a single use is sometimes used in a subsequent dispensing operation to place impressioning material in a second impression tray. However, a previously used cartridge often does not contain a sufficient quantity of the components to fill a second tray, and as a result the dispensing operation must be interrupted once the first cartridge is empty to replace the empty cartridge with a second cartridge. Unfortunately, there is often only a relatively short working time that is available for the practitioner to place and properly position the tray with the impressioning material in the oral cavity once the components are mixed and dispensed into the tray. If the dispensing operation is interrupted to remove an empty cartridge and install a full cartridge in the applicator, such an interruption necessarily reduces the amount of time available for the practitioner to place and properly orient the impression tray in the oral cavity.

As a consequence, many practitioners prefer to start with a new dispensing cartridge in the applicator each time that an impressioning tray is to be filled in order to avoid any reduction in the amount of time available to place and orient the tray in the oral cavity. Partially empty cartridges can be discarded, but such practice represents waste.

Similar problems exist in other fields where dual chamber dispensing cartridges are used. For example, when dispensing a fast-setting epoxy used in a manufacturing process, the user may not have sufficient time to replace an empty cartridge with a full cartridge during a dispensing operation. In such circumstances, the user may opt to start with a new cartridge at the beginning of each procedure, and discard any partially empty cartridges as waste.

Clearly, there exists a need in the art for a device that prevents such waste so that substantially all of the components in a cartridge can be used. Preferably, such a device would not interrupt a dispensing procedure so that the working time of the dispensed material is not reduced.

SUMMARY OF THE INVENTION

The present invention concerns a device for consolidating compositions contained in partially filled dual chamber dispensing cartridges. The device includes a body having a pair of side-by-side passages, and a first coupler for releasably coupling the body to a first dual chamber dispensing cartridge in an orientation wherein the passages are in communication with side-by-side outlets of the first cartridge. The device also includes a second coupler for releasably coupling the body to a second dual chamber dispensing cartridge in an orientation wherein the passages are in communication with side-by-side outlets of the second cartridge. The body also includes at least two sealing sections for sealing contact with the first cartridge and the second cartridge when the first cartridge and the second cartridge are coupled by the first coupler and the second coupler to the body.

The device of the invention serves to fill a new, empty cartridge or to refill or partially refill a cartridge that has been previously used. In practice, the device may be used to sequentially connect several partially empty cartridges to a selected host cartridge until the host cartridge is substantially or completely filled with components. The host cartridge can then be used to dispense without interruption a quantity of components that is substantially equal to the quantity of components contained in a new cartridge. The invention serves to greatly reduce waste of the components because substantially all of the components of each cartridge can be beneficially used without adversely affecting the dispensing procedure.

DETAILED DESCRIPTION OF THE PREFERRED EMBODIMENTS

Figures 1, 2:
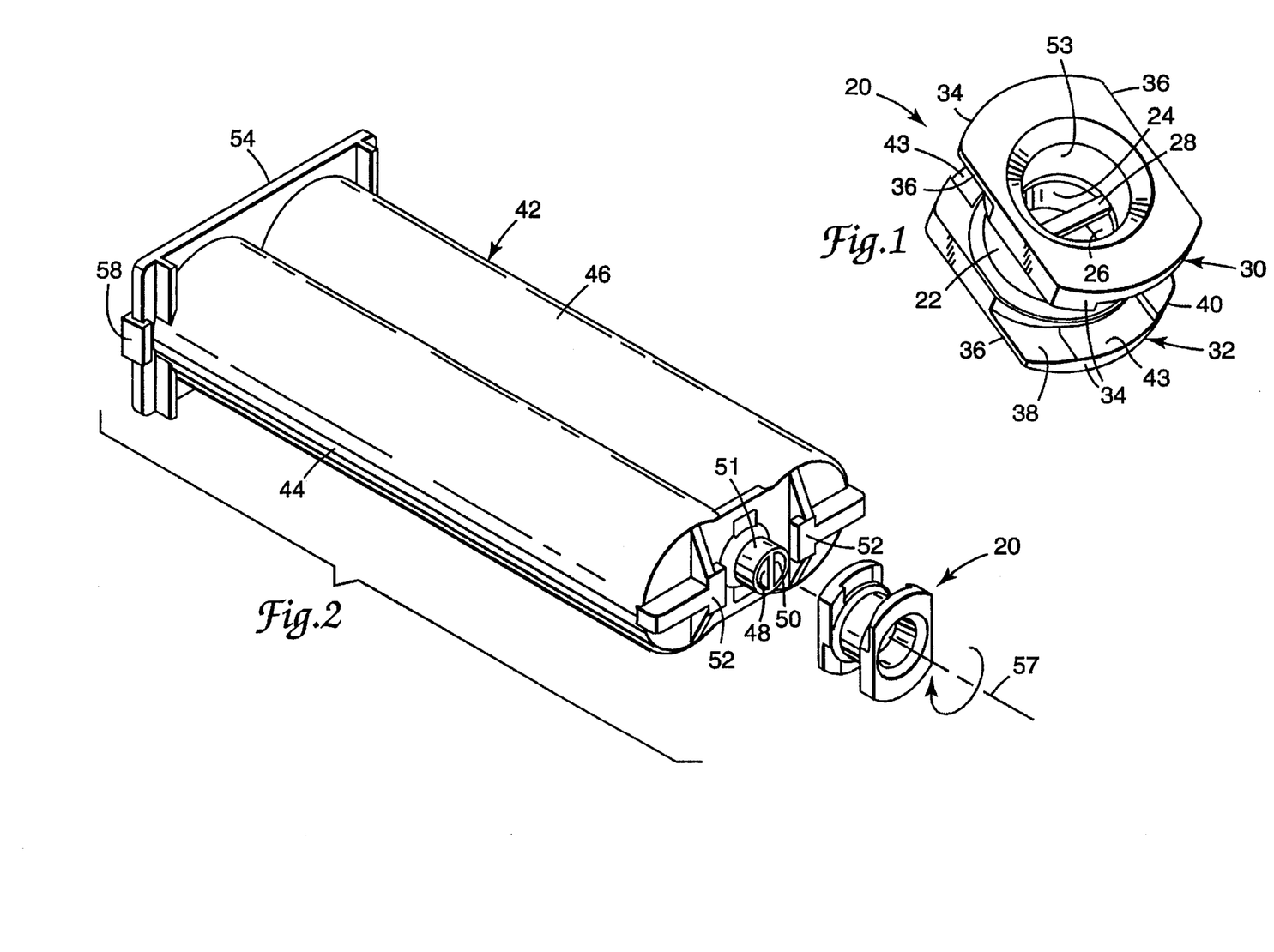
FIG. 1 is a perspective view of a dual chamber dispensing cartridge refilling device according to one embodiment of the invention.
FIG. 2 is a reduced perspective view of the device illustrated in FIG. 1 along with one of two dual chamber dispensing cartridges that may be coupled together by the device.
Figure 4:
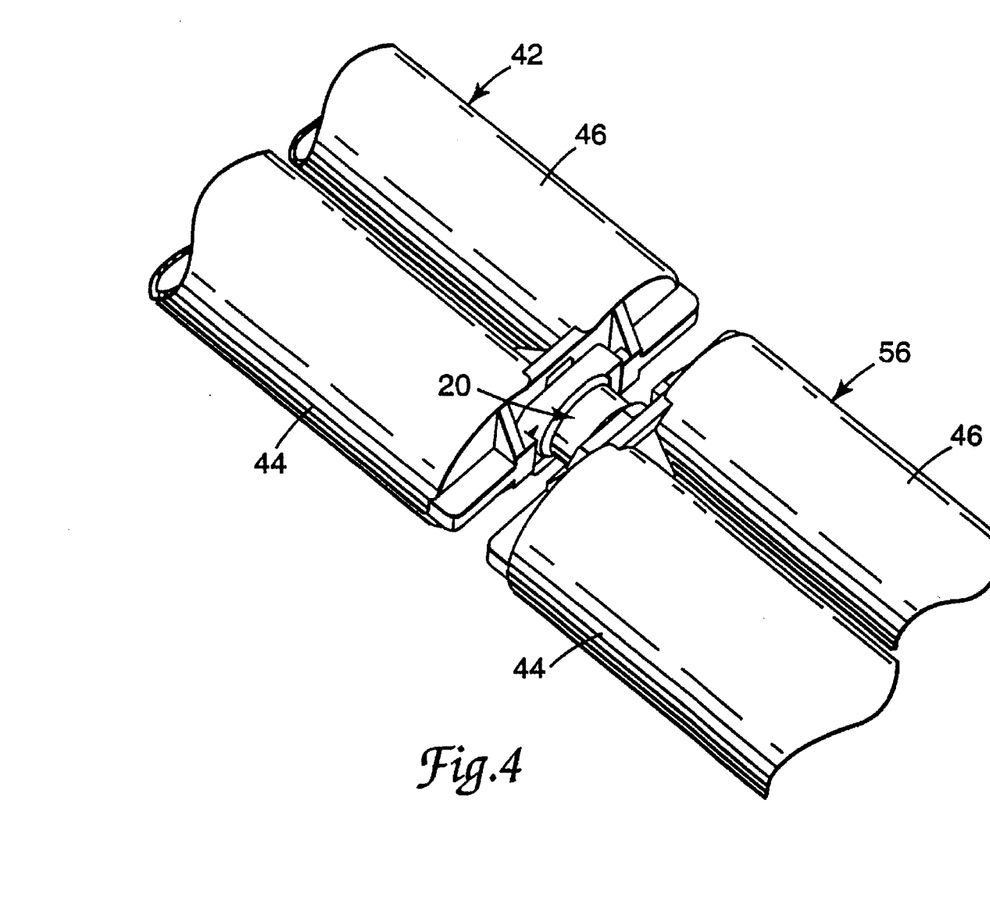
FIG. 4 is a fragmentary, reduced perspective view somewhat similar to FIG. 2 except that a second cartridge has been added and the two cartridges have been coupled to the refilling device.

A device for consolidating compositions contained in partially filled dual chamber dispensing cartridges is designated broadly by the numeral 20 in FIGS. 1, 2 and 4 according to one embodiment of the invention. The device 20 in the particular embodiment shown includes a hollow, cylindrical body 22 that has a first passage 24 and a second passage 26. The passages 24, 26 are separated by a dividing wall 28 that extends across the middle of the interior of the body 22 from one side to another.

The passages 24, 26 are in side-by-side relation to each other and have a generally D-shaped configuration. The dividing wall 28 is recessed on opposite sides from respective ends of the hollow body 22. A chamfered wall section 53 (see FIG. 1) is located on each side of the dividing wall 28 between the dividing wall 28 and respective ends of the body 22.

The device 20 also includes a first coupler 30 that is connected to one end of the body 22 and a second coupler 32 that is connected to an opposite end of the body 22. Each of the couplers 30, 32 includes two opposed, curved flanges 34 having a curved outer edge. The curved flanges 34 of each coupler 30, 32 are integrally interconnected to each other by respective pairs of straight flanges 36 having straight outer edges.

Preferably, and as illustrated for example in FIG. 1, each of the curved flanges 34 has an inclined or ramped surface 38 and a non-inclined or "level" surface 43 that face the curved flange 34 of the other coupler 30, 32. In addition, each of the curved flanges 34 includes a stop portion 40 that is located next to the end of the respective level surface 43 and is adjacent a corresponding straight flange 36. When the device 20 is held in a vertical orientation wherein an imaginary central reference axis of the body 22 extends in a vertical direction and when the viewer is looking toward the curved outer edge of the curved flanges 34, the ramped surface 38 of the lowermost curved flange 34 is inclined in an upwardly direction as the right side of such curved flange 34 is approached, and the stop portion 40 is located next to the upper end and to the right of such ramped surface 38.

Preferably, the body 22 and the couplers 30, 32 are integrally molded of a rigid, durable material that does not degrade or react with compositions passing through the passages 24, 26. Suitable materials include synthetic resinous materials such as polyethylene or polypropylene.

The device 20 is adapted for use with a pair of dual chamber dispensing cartridges such as the dispensing cartridge 42 illustrated in FIG. 2. Such cartridges are well known in the art (see, e.g., U.S. Pat. No. 5,236,108) and include a first and second elongated barrel or container 44, 46. The first container 44 has an inner cylindrical chamber (not shown) that is in communication with a first outlet 48 located at the front of the cartridge 42. Similarly, the second container 46 includes an inner cylindrical chamber in communication with a second, front outlet 50. Both of the outlets 48, 50 are contained within a cylindrical, protruding neck or outlet conduit 51 of the front end of the cartridge 42. As shown in FIG. 2, the outlet conduit 51 includes a central baffle that separates the outlets 48, 50 from each other. The outer wall of the outlet conduit 51 includes a front cylindrical surface and a rear chamfered wall section located between the front cylindrical surface and the front end of the containers 44, 46.

The front end of the cartridge 42 also includes a pair of opposed tabs 52 that are located on opposite sides of the outlet conduit 51 and extend toward each other. Each tab 52 is integrally joined to a pair of triangular reinforcing wall sections that extend parallel to the baffle. Each tab 52 is also integrally connected to a rectangular reinforcing wall section that extends perpendicularly to the baffle.

The cartridge 42 also has a rectangular rear flange 54 that is adapted to releasably fit into a cartridge receptacle of an applicator (not shown). The applicator may be hand powered or driven by an electric motor or pneumatic power as described above.

Each chamber of the cartridge 42 is adapted to contain one component or composition of a two component material such as dental impressioning material. Each chamber of the cartridge 42 is provided with a piston (not shown) for engagement with movable plungers of the applicator. As the plungers advance and move the pistons toward the front end of the cartridge 42, components in the chambers are directed through respective outlets 48, 50 in separate, spaced apart streams.

The cartridge 42 may be any one of a number of commercially available cartridges such as the cartridge available with purchase of 3M's silicone dental impressioning material (catalog no. 7302H). Such cartridges are often integrally molded of a synthetic resinous material such as polypropylene; however, other materials such as nylon, polyethylene or acetal may also be employed.

A second cartridge 56 is illustrated in FIG. 4. The second cartridge 56 is identical to the first cartridge 42 and as such a detailed description of the second cartridge 56 need not be provided. In FIG. 4, elements of the second cartridge 56 that are designated by numerals are identical to like-numbered elements of the first cartridge 42.

In use, the device 20 is moved toward the first cartridge 42 along a reference axis 57 while being held in the orientation that is shown in FIG. 2. In that orientation, the straight edges of the straight flanges 36 are parallel with the straight, inwardly facing edges of the tabs 52 of the first cartridge 42. The distance between the straight outer edges of the straight flanges 36 of the first coupler 30 is somewhat less than the distance between the straight inner edges of the tabs 52 such that the flanges 36 move past the tabs 52 at the same time that the protruding outlet conduit 51 surrounding the outlets 48, 50 moves into the interior of the body 22.

Once the circular, outer edge of the cartridge outlet conduit 51 contacts the chamfered wall section 53 of the body 22, the device 20 is rotated by hand relative to the first cartridge 42 in a direction as indicated by the arrow in FIG. 2 about the reference axis 57. The reference axis 57 is collinear with the central axis of the body 22 and is parallel to the longitudinal axes of the containers 44, 46. As the device 20 rotates about the axis 57, the curved flanges 32 pass beneath the overhanging tabs 52, and the ramped surfaces 38 cause the chamfered wall section 53 next to the first coupler 30 to be pressed in snug, sealing engagement with the outer edge of the outlet conduit 51. The device 20 is further rotated about the axis 57 in such fashion as the level surfaces 43 slide beneath the tabs 52 until the stop portions 40 of the first coupler 30 engage the sides of the tabs 52 and prevent further rotation.

The dividing wall 28 of the device 20 is aligned in coplanar fashion with the outlet baffle of the first cartridge 42 when the device 20 is fully installed on the first cartridge 42 such that the stop portions 40 of the first coupler 30 are in contact with the tabs 52. The outer edge of the dividing wall 28 facing the first cartridge 42 is spaced inwardly from the adjacent outer edge of the device 20 a distance to enable the device 20 to be fully seated on the protruding outlet conduit 51, and yet also enable the adjacent outer edge of the dividing wall 28 to be in firm, leak-resistant contact with the front edge of the baffle between the outlets 48, 50.

Next, the second cartridge 56 is moved toward the device 20 while being held in such an orientation that the straight, facing wall sections of the tabs 52 of the second cartridge 56 are parallel with the straight outer edges of the straight flanges 36 of the second coupler 32. The outlet conduit 51 of the second cartridge 56 is then moved into the interior of the body 22 until the interior, chamfered wall section 53 next to the second coupler 32 contacts the outer circular edge of the protruding outlet conduit 51 of the second cartridge 56.

Subsequently, the second cartridge 56 is turned about the axis 57 in the direction indicated by the arrow in FIG. 2 relative to the first cartridge 42 such that the curved flanges 34 of the second coupler 32 move beneath the tabs 52 of the second cartridge 56 in a manner identical to the locking, coupling movement of the first coupler 30 as described above when the device 20 is connected to the first cartridge 42. When the second cartridge 56 is fully and securely coupled to the device 20, the second cartridge 56 is aligned with the first cartridge 42 in the manner shown in FIG. 4 wherein the central, longitudinal axes of the first containers 44 are collinear relative to each other and the central, longitudinal axes of the second containers 46 are collinear relative to each other. Furthermore, when the cartridges 42, 56 are both fully coupled to the device 20, the first outlets 48 of the cartridges 42, 56 are in communication only with the first passage 24 and the second outlets 50 of the cartridges 42, 56 are in communication only with the second passage 26.

Next, an applicator is connected to one of the cartridges 42, 56, depending on which cartridge is designated as the host cartridge. If, for example, the first cartridge 42 is selected as the host cartridge to be refilled, the applicator is connected to the second cartridge 56. Typically, although not necessarily, the applicator has a receptacle as mentioned above to receive the rear cartridge flange 54 of the second cartridge 56. The applicator also includes plungers or the like to advance the cartridge pistons.

Figure 3:
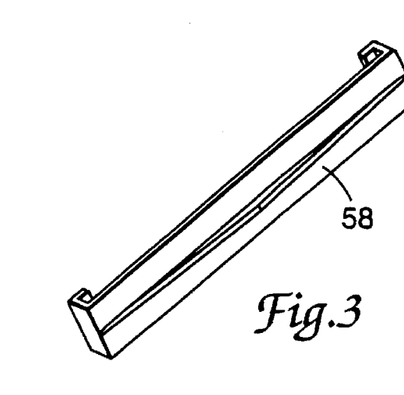
FIG. 3 is a perspective view of a retaining clip alone that is also illustrated in FIG. 2.

Preferably, a stop clip 58 (FIGS. 2 and 3) is placed over the rear flange 54 of the first cartridge 42 before the plungers of the applicator are advanced to move the pistons of the second cartridge 56. The stop clip 58 has a pair of opposed "U"-shaped end sections that complementally engage opposite sides of the rear flange 54. The stop clip 58 prevents the pistons of the first cartridge 42 from moving past the open, rear ends of the containers 44, 46 and detaching from the cartridge 42 while the components are introduced into the first cartridge 42. The stop clip 58 is preferably made of a resilient material such as injection-molded plastic or spring steel that can be readily attached and detached from the rear flange 54 as needed.

The applicator is then operated to advance the plungers and move the pistons of the second cartridge 56 forwardly and toward the first cartridge 42. As the pistons so move, the components within the second cartridge 56 are expelled through the outlets 48, 50 of the second cartridge 56, through the passages 24, 26 of the body 22 and then through respective outlets 48, 50 of the first cartridge 42 and into the containers 44, 46 of the first cartridge 42. Preferably, the plungers of the applicator are advanced sufficiently to direct essentially all of the components remaining in the second cartridge 56 through the device 20 and into the first cartridge 42.

As the components pass from the second cartridge 56 into the first cartridge 42, the passages 24, 26 function to keep the components separated so that cross-contamination and possible reaction of the components cannot occur. The size and configuration of the dividing wall 28, the baffle, the outer edge of the outlet conduit 51 and the chamfered wall section 53 provide sealing contact between the body 22 and the cartridges 42, 56 when coupled together in the manner shown in FIG. 4 so that cross-contamination of the components or leakage of the components to areas external of the device 20 is essentially prevented.

Once the components in the second cartridge 56 have been emptied into the first cartridge 42 (or, alternatively, once the pistons of the first cartridge 42 have come into contact with the stop clip 58), advancement of the plungers of the applicator is interrupted. If, for example, the second cartridge 56 is now empty, the second cartridge 56 is removed from the applicator. The second cartridge is also detached from the device 20 by turning the second cartridge 56 in a direction opposite to the arrow in FIG. 2 relative to the first cartridge 42 until the straight outer edges of the straight flanges 36 are aligned with the straight, facing edges of the tabs 52 of the second cartridge 56. The second cartridge 56 is then moved away from the device 20 along axis 57 (FIG. 2). The above procedure is then repeated with another partially filled cartridge in place of the second cartridge 56.

On the other hand, if the first cartridge 42 is filled before the components have been completely expelled from the second cartridge 56, the first cartridge 42 is detached from the device 20 by rotating the first cartridge 42 relative to the device 20 and the second cartridge 56 in a direction opposite to that of the arrow shown in FIG. 2. The first cartridge 42 is then uncoupled from the device 20 and another cartridge that is empty or partially empty is reinstalled in its place.

Although not shown, an alignment or orienting section may optionally be provided to insure that the device 20 cannot be connected to the first cartridge 42 or the second cartridge 56 unless each first container 44 is ultimately in alignment with the first passage 24 and each second container 56 is ultimately in alignment with the second passage 26. The orienting section may take any of several forms. One possible orienting section could be constructed by providing the curved flanges 34 of each coupler 30, 32 with different lengths in directions radially of the central axis of the body 22, and also providing cartridges with tabs 52 that are matingly offset corresponding distances from the outlet conduit 51. In such structure, the tabs 52 prevent coupling of the cartridges 42, 56 to the device 20 unless the containers 44, 46 of one cartridge have been oriented for ultimate proper alignment with the containers 44, 46 of the other cartridge as well as with the passages 24, 26 of the body 22.

A dual chamber dispensing cartridge refilling device 20a according to a second embodiment of the invention is illustrated in FIGS. 5–8. The device 20a includes a retainer 21a that is shown alone in FIG. 5 and an adapter body 22a that is shown alone in FIG. 6.

Figure 5:
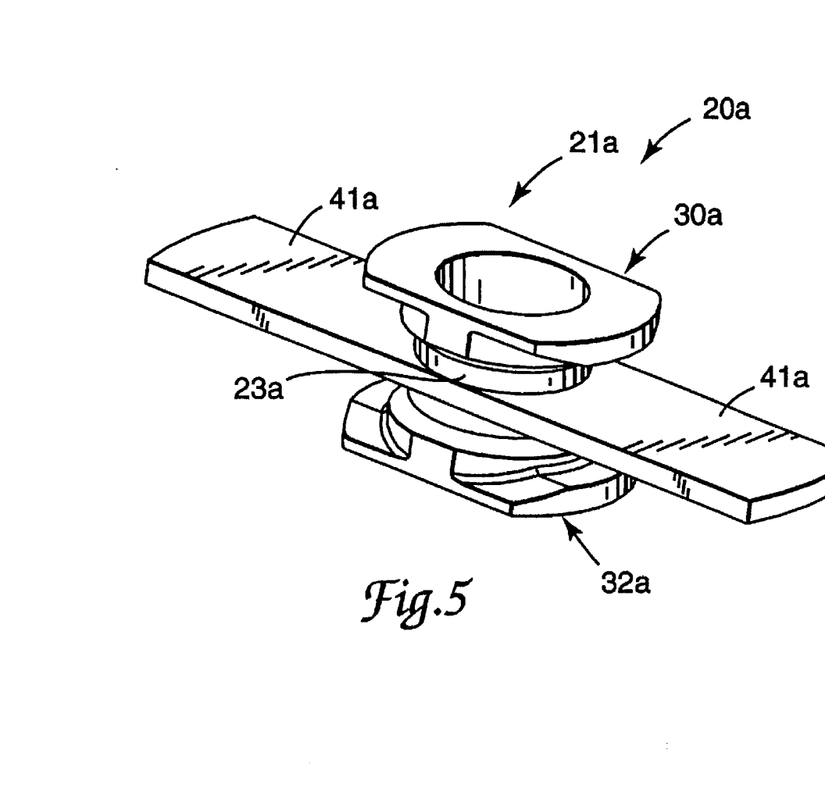
FIG. 5 is a perspective view of a retainer that is part of a dual chamber dispensing cartridge refilling device according to another embodiment of the invention.

The retainer 21a includes a central member 23a that is hollow and cylindrical, and lacks a central dividing wall (such as dividing wall 28 described above). A first coupler 30a and a second coupler 32a are integrally connected to opposite ends of the member 23a. Each of the couplers 30a, 32a includes two curved flanges and two straight flanges that are identical to the flanges 34, 36 respectively described above. Preferably, but not necessarily, each curved flange includes a ramped surface, a level surface and a stop portion that are identical to the ramped surface 38, the level surface 43 and the stop portion 40 respectively.

The retainer 21a also includes a pair of arms 41a that are connected to the member 23a and extend outwardly away from each other in opposite directions. As depicted in FIG. 5, the arms 41a extend in a direction that is parallel to the straight outer edges of the straight flanges, although other directions are also possible. Moreover, while two arms 41a are shown, the retainer 21a could alternatively have a greater number or a smaller number of such arms.

Figure 6:
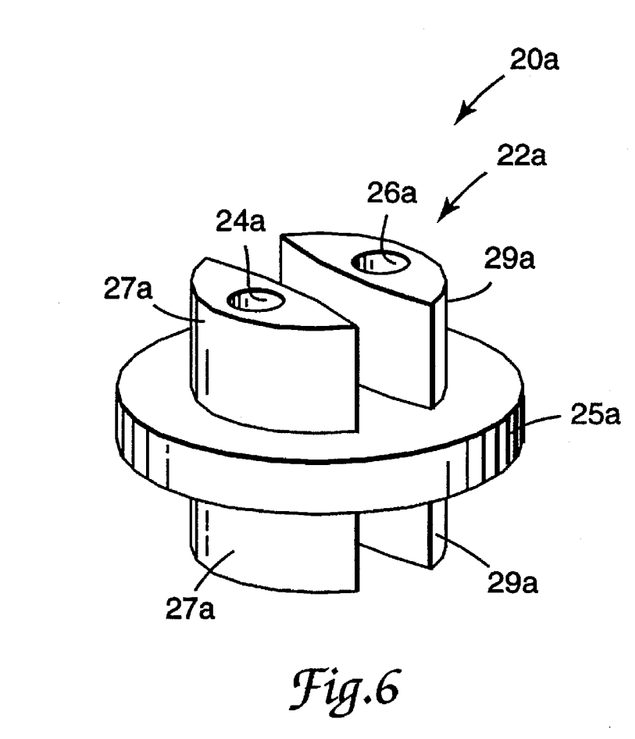
FIG. 6 is an enlarged perspective view of an adapter body that is also part of the refilling device described in connection with the retainer shown in FIG. 5.

Referring now to FIG. 6, the adapter body 22a includes a central, circular plate 25a and two pairs of projections 27a, 29a. The projections 27a are aligned with each other, and a first passage 24a extends through the projections 27a as well as through the plate 25a. Similarly, the projections 29a are aligned with each other and a second passage 26a extends through the two projections 29a as well as through the plate 25a.

Figure 7:
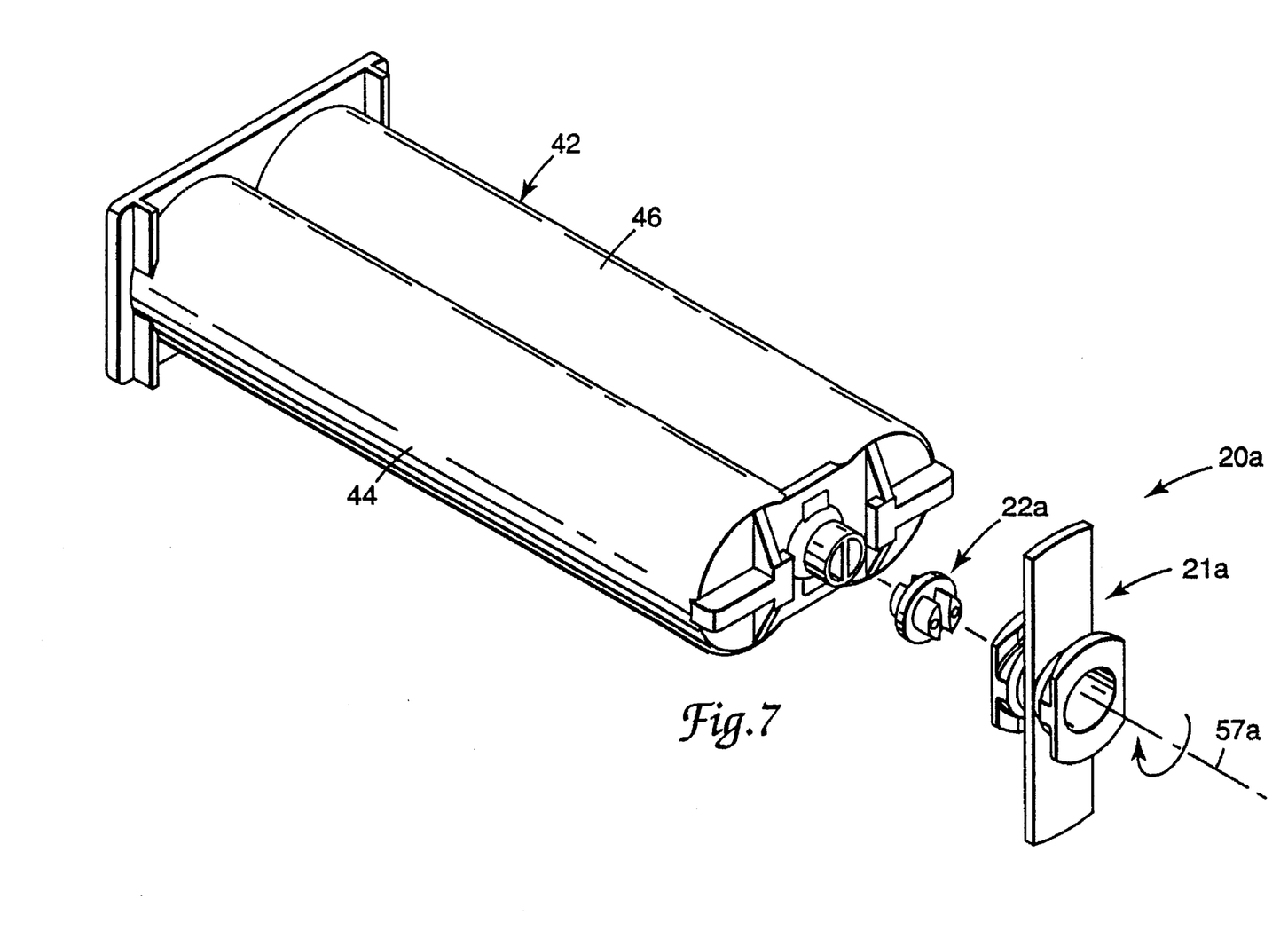
FIG. 7 is a reduced perspective view of the retainer shown in FIG. 5 and the adapter body shown in FIG. 6 along with a dual chamber dispensing cartridge, depicting the retainer, adapter body and cartridge as they might appear before assembly to one another.

In use, the body 22a is aligned with the first cartridge 42 in the manner shown in FIG. 7 such that the projections 27a, 29a on one side of the plate 25a are aligned with the first outlet 48 and the second outlet 50 respectively. The body 22a is then moved toward the first cartridge 42 and along reference axis 57a such that the projections 27a, 29a on the side of the plate 25a facing the first cartridge 42 enter the outlets 48, 50 respectively. When the projections 27a, 29a are fully inserted into the outlets 48, 50 of first cartridge 42, the facing wall section of the plate 25a flatly contacts the outer edge of the outlet conduit 51 including the outer edge of the baffle.

Next, the retainer 21a is also moved toward the first cartridge 42 along axis 57a while held in the orientation shown in FIG. 7. In such an orientation, the straight flanges are parallel to the facing edges of the tabs 52 in a manner similar to that described above in connection with assembly of the embodiment shown in FIGS. 1, 2 and 4. As the retainer 21a moves closer to the cartridge 42, the central member 23a moves to a position surrounding the body 22a.

Next, the second cartridge 56 is moved toward the body 22a while being held in an orientation wherein the longitudinal axes of the containers 44, 46 of the first cartridge are collinear with the longitudinal axes of the containers 44, 46 respectively of the second cartridge. The second cartridge 56 is moved toward the body 22a until the projections 27a, 29a facing the second cartridge 56 are fully inserted into the outlets 48, 50 of the second cartridge 56 and the facing wall section of the plate 25a flatly contacts the outer edge of the outlet conduit 51 (including the outer edge of the baffle) of the second cartridge 56.

Figure 8:
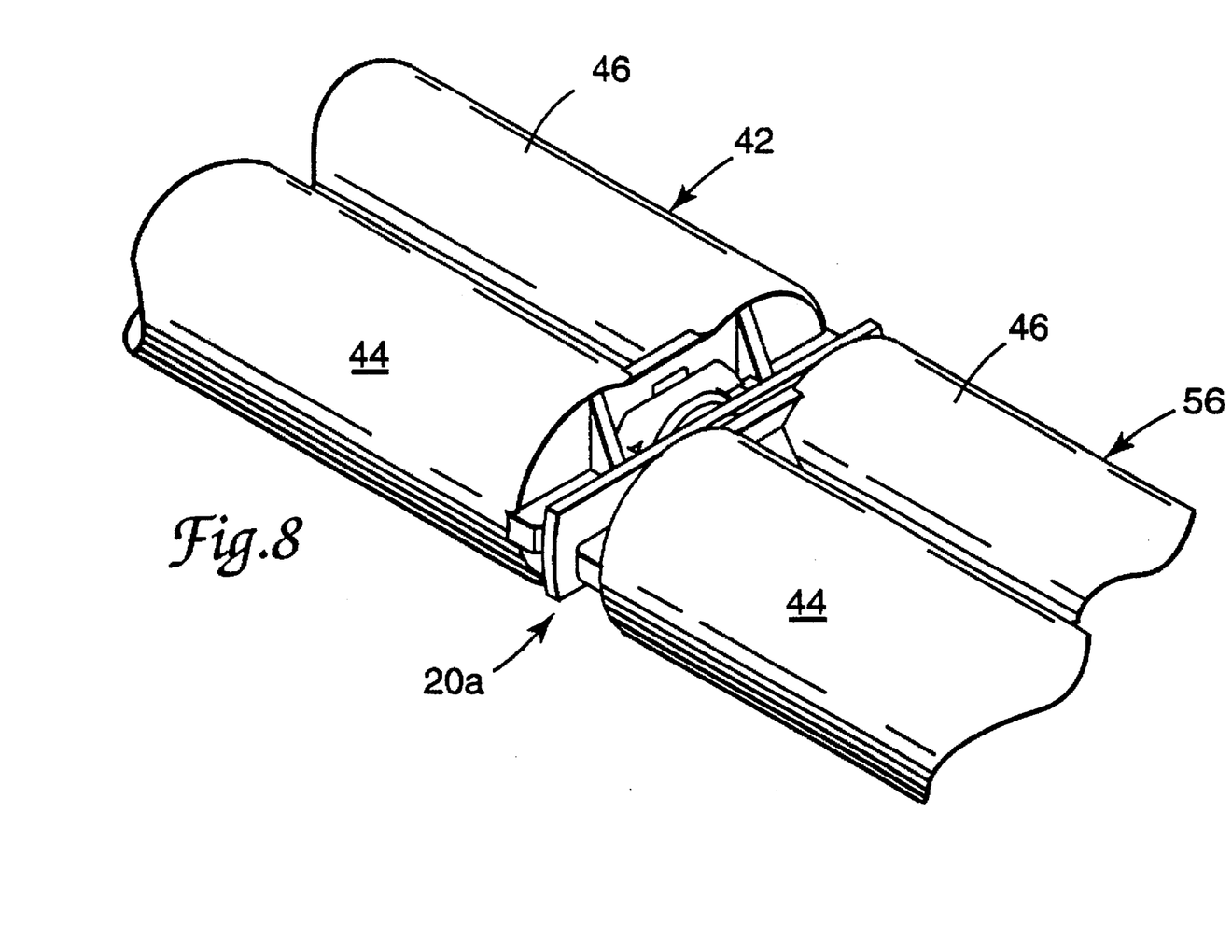
FIG. 8 is a fragmentary, reduced perspective view somewhat similar to FIG. 7 except that a second dual chamber dispensing cartridge has been added and the retainer and adapter body have been fully coupled to the front ends of both cartridges.

The retainer 21a is then turned by grasping the arms 41a and rotating the retainer 21a relative to the first cartridge 42 and the second cartridge 56 about the axis 57a. The axis 57a is collinear with a central axis of the retainer 21a and the body 22a, and is parallel to the central, longitudinal axes of the containers 44, 46 of both cartridges 42, 56 when connected to the body 22a. The first coupler 30a operates in a manner identical to that described above in connection with the embodiment shown in FIGS. 1, 2 and 4. Once the arms 41a are turned 90 degrees and extend in the direction that is shown in FIG. 8, the retainer 21a is securely coupled to the containers 42, 56.

Subsequently, an applicator is connected to one of the cartridges 42, 56 in order to expel components remaining in such cartridge to the other cartridge in a fashion similar to that described above in connection with the embodiment shown in FIGS. 1, 2 and 4. Additionally, a stop clip such as the stop clip 58 shown in FIGS. 2–3 may be provided to prevent undue rearward movement of the pistons of the host cartridge. Once the refilling operation has been completed, the applicator is removed and the cartridges 42, 56 are uncoupled from each other as well as from the refilling device 20a by reversing the steps set out above.

Preferably, retainer 21a including the cylindrical member 23a, the couplers 30a, 32a and the arms 41a are integral and made of a relatively rigid material that does not react with components in the cartridges 42, 56. Suitable materials include metals such as type AISI 302 stainless steel, and plastics such as polysulfone, available from Amoco under the trademark "UDEL".

The body 22a is preferably integrally molded of an elastomeric material that does not react with the components in the cartridges 42, 56. Preferably, the elastomeric material does not contain any sulfur compounds that might otherwise hinder the effectiveness of catalysts used in dental impressioning material. Suitable elastomerics include polyurethane and silicone rubbers.

The adapter body 22a is preferably resilient and has a relatively low modulus of elasticity so that the body 22a readily provides a leak-resistant seal between the device 20a and the cartridges 42, 56. The wall sections of the plate 25a that are in flat contact with the outer circular edge of the outlet conduit 51 as well as with the outer edge of the baffle function as sealing sections for preventing escape of the components during passage from one cartridge to the other. The thickness of the plate 25a is selected to ensure that the plate 25a is slightly compressed between the outlet conduits 51 of the cartridges 42, 56 when the cartridges 42, 56 are coupled together by the device 20a in the manner depicted in FIG. 8.

Preferably, the retainer 21a includes an inner circular shoulder that blocks passage of the body 22a completely through the member 23a, and instead allows the body 22a to be removed through only one of the two open ends of the member 23a. The shoulder is an advantage when the body 22a is between the shoulder and the host cartridge, because the body 22a will stay connected to the host cartridge when the other cartridge is detached so long as the retainer 21a also remains connected to the host cartridge.

Optionally, the device 20a includes means for retaining the body 22a in the retainer 21a to facilitate handling and assembly and to prevent the body 22a from becoming misplaced. Such means could comprise, for example, a pair of spaced apart annular retaining rings provided in the interior of the member 23a instead of the shoulder mentioned above, with the plate 25a received in the space between the rings. Such means, however, should enable rotation of the body 22a relative to the retainer 21a as the retainer 21a is turned relative to the cartridges 42, 56, so that the projections 27a, 29a are not damaged and remain in place in the outlets 48, 50 of any cartridge coupled to the retainer 21a.

Figures 9, 10:
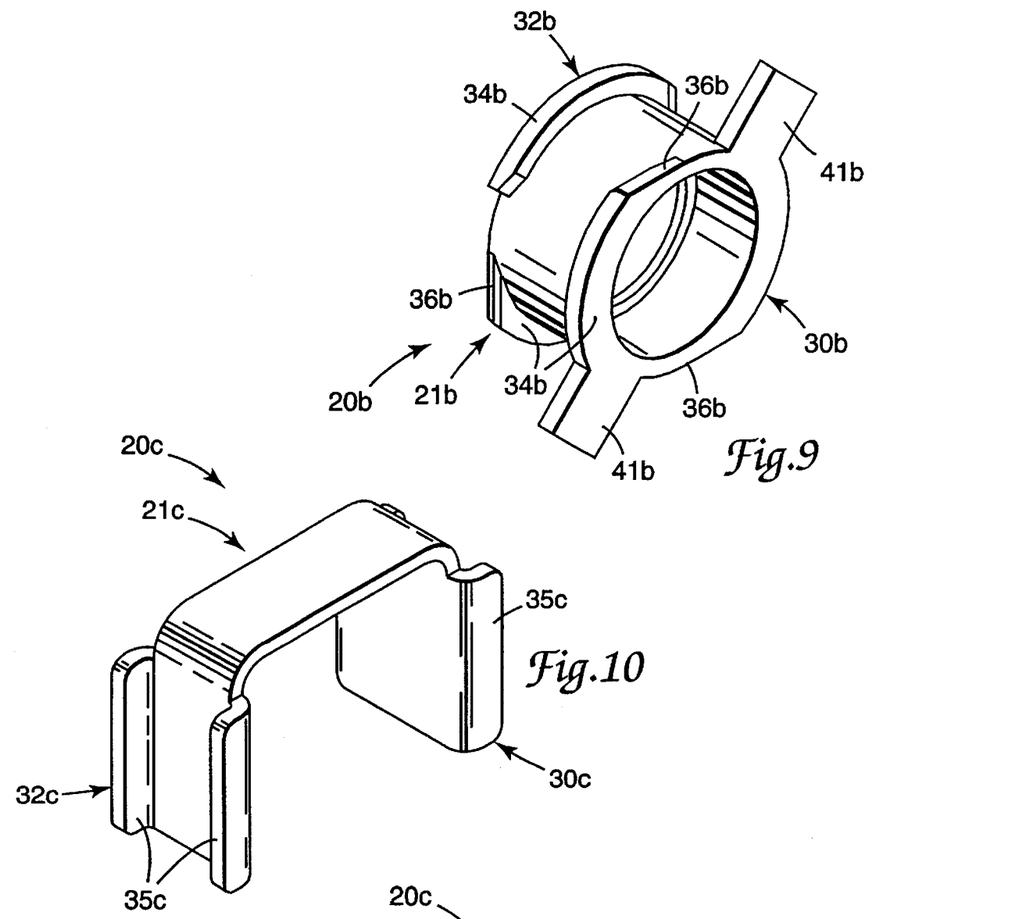
FIG. 9 is a perspective view of a retainer of a dual chamber dispensing cartridge refilling device according to another embodiment of the invention.
FIG. 10 is a perspective view of a retainer of a dual chamber dispensing cartridge refilling device according to yet another embodiment of the invention.

An alternative retainer 21b is illustrated in FIG. 9 according to another embodiment of the invention. The retainer 21b is similar to the retainer 21a with the exception of the features noted below.

More particularly, the retainer 21b has a first coupler 30b and a second coupler 32b that is oriented in a somewhat different rotative position relative to the first coupler 30b with reference to a central axis passing through the hollow interior of the retainer 21b. Any one of a number of different rotative orientations can be provided. In the embodiment shown in FIG. 9, the second coupler 32b is oriented approximately 90 degrees about its central axis relative to the first coupler 30b, such that straight outer edges of straight flanges 36b of the first coupler 30b extend in a direction perpendicular to the straight outer edges of straight flanges 36b of the second coupler 32b.

The couplers 30b, 32b include curved flanges that each have a small ramped surface on each end for engagement with the tabs 52, but the couplers lack stop portions similar to the stop portions 40 described above. As such, the retainer 21b may be detached from the cartridges 42, 56 by rotation of the retainer 21b in either direction about its central axis. As an alternative, however, the curved flanges of the couplers 30b, 32b may include larger ramped surfaces and also include stop portions identical to the ramped surfaces 38 and the stop portions 40 described above.

The retainer 21b also has a pair of arms 41b that are connected to flanges 34b, 36b of the first coupler 30b. The arms 41b extend away from each other and at a non-zero angle relative to the straight outer edges of straight flanges 36b of the couplers 30b, 32b. In the embodiment shown, the arms 41b extend at an angle of approximately 45 degrees relative to the straight outer edges of the straight flanges 36b of both the couplers 30b, 32b, although other orientations are, of course, possible.

Figure 11:
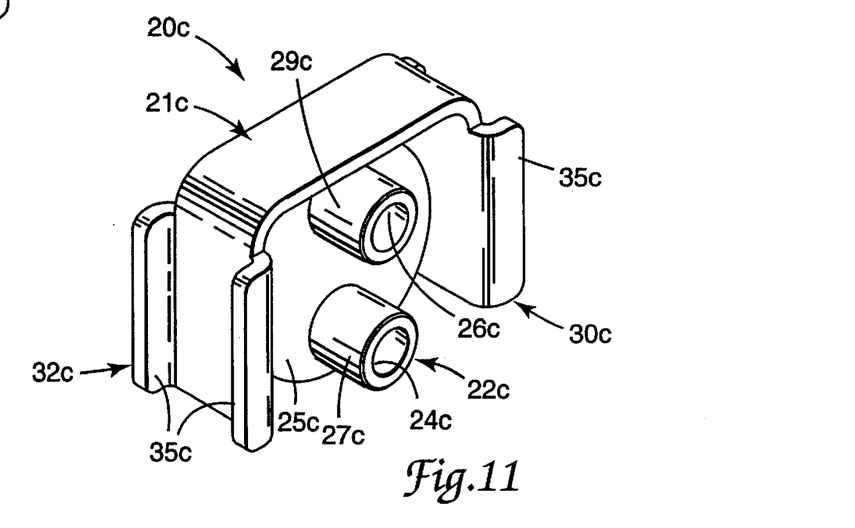
FIG. 11 is a perspective view of the retainer shown in FIG. 10 along with an adapter body that is somewhat different than the adapter body shown in FIG. 6.

The embodiment of the invention that is illustrated in FIGS. 10 and 11 concerns a dual chamber dispensing cartridge refilling device 20c that includes a retainer 21c that is shown in FIG. 10 alone as well as an adapter body 22c that is shown only in FIG. 11. The retainer 21c is in the form of a clip having an overall "U"-shaped configuration.

The retainer 21c includes a first coupler 30c having a pair of flanges 35c that extend away from each other. The retainer 21c also includes a second coupler 32c having a pair of identical flanges 35c that also extend away from each other. The retainer 21c is preferably integrally made of a stamped section of sheet metal, although alternatively other materials such as the materials described above in connection with the retainer 21a could be used.

The body 22c is somewhat similar to the body 22a, in that the body 22c has a first elongated passage 24c, a second elongated passage 26c and a plate 25c. The body 22c also has projections 27c, 29c surrounding the passages 24c, 26c on one side of the plate 25c. Although not shown, a similar set of projections is provided on the opposite side of the plate 25c. For exemplary purposes, the projections 27c, 29c have an external cylindrical shape, although it should be understood in this regard that the projections could also have other shapes such as a generally "D"-shaped external configuration similar to the shape of the projections 27a, 29a illustrated in FIG. 6.

The projections 27c, 29c are of a certain shape and are spaced apart a distance to match the shape and spacing of outlets of other types of dual chamber dispensing cartridges. For example, the projections 27c, 29c of the body 22c may have a shape matching the outlet ports of the dispensing cartridge illustrated in U.S. Pat. No. 5,333,670. Of course, many other shapes, sizes and spacings are also possible.

In use of the embodiment illustrated in FIGS. 10 and 11, the projections 27c, 29c of the body 22c are placed in the outlets of two dispensing cartridges that face each other. While the cartridges and the body 22c are held in such an orientation, the retainer 21c is moved in a direction that is perpendicular to the longitudinal axes of the passages 24c, 26c. While the retainer 21c is moving in such a direction, the flanges 35c pass beneath tabs (such as tabs 52) of the cartridges in order to couple the device 20c to the two cartridges.

The body 22c is preferably made of an elastomeric material similar to the materials described above in connection with the body 22a. The body 22c provides a seal between the outlet conduits of the dispensing cartridges once the retainer 21c has been installed in place. After the components in one cartridge have been transferred to the other cartridge, the device 20c is uncoupled from the cartridges by moving the retainer 21c away from the body 22c in a direction that is also perpendicular to the longitudinal axes of the passages 24c, 26c until the flanges 30c are released from the tabs of the cartridges.

FIGS. 12–15 illustrate a dual chamber dispensing cartridge refilling device 20d that is constructed according to another embodiment of the invention. The device 20d is shown alone in FIGS. 12 and 13 and includes a body 22d having an elongated, generally cylindrical shape with two spaced apart plates 25d. A pair of projections 27d, 29d extends outwardly from one plate 25d, and a similar pair of projections 27d, 29d extends outwardly from the other plate 25d. The projections 27d, 29d are essentially identical to the projections 27a, 29a described above in that they are each adapted to fit within the confines of spaced apart outlets of a protruding outlet conduit of a dual chamber dispensing cartridge such as cartridges 42, 56. A pair of spaced apart, non-communicating, generally "D"-shaped passages 24d, 26d (FIG. 12) extends through the projections 27d, 29d respectively as well as through the interior of the body 22d.

Figure 12:
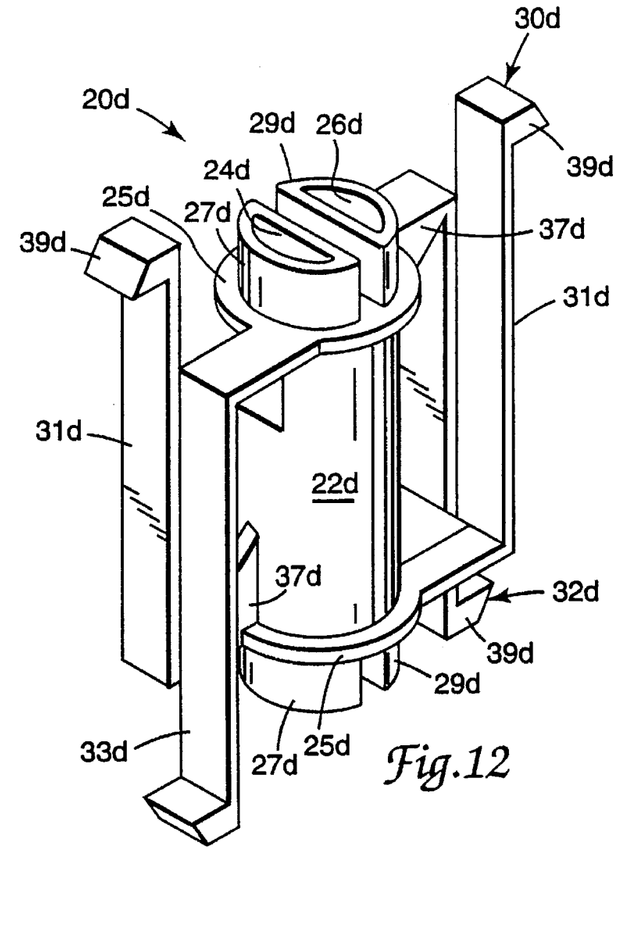
FIG. 12 is a perspective view of a unitized dual chamber dispensing cartridge refilling device according to still another embodiment of the invention.
Figure 13:
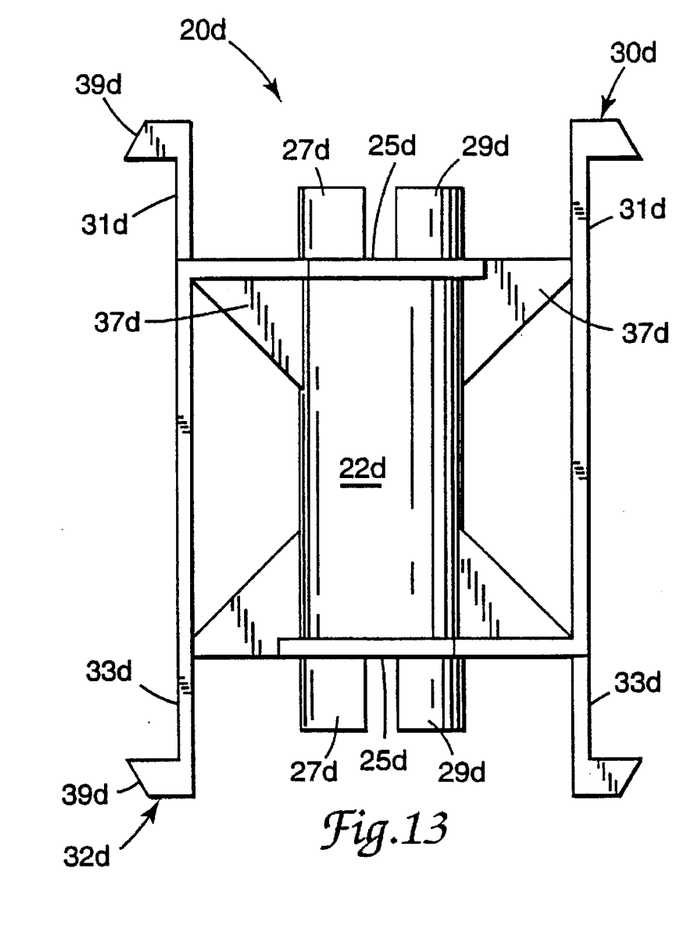
FIG. 13 is a front elevational view of the refilling device illustrated in FIG. 12.

A first coupler 30d of the device 20d includes a pair of "L"-shaped legs 31d that are integrally connected to one of the plates 25d and extend past the other plate 25d. A second coupler 32d of the device 20d has a similar pair of legs 33d that are integrally connected to the opposite plate 25d and extend toward the plate 25d that is integrally connected to the legs 31d. A triangular brace 37d integrally connects the body 22d and a first, adjacent portion of the legs 31d, 33d that extends outwardly in a radial direction from the body 22d.

Each of the legs 31d, 33d includes an outermost hook 39d that is adapted to fit behind tabs of a dual chamber dispensing cartridge such as tabs 52 of the cartridges 42, 56. A second portion of the legs 31d, 33d extends between the hooks 39d and the first portion. The second portion of the legs 31d, 33d, being not directly connected to the braces 37d, is flexible and can be readily shifted inwardly by finger pressure or otherwise toward the body 22d when desired. Each hook 39d includes an outer chamfered wall for engagement with the tabs of the dispensing cartridges.

Figure 14:
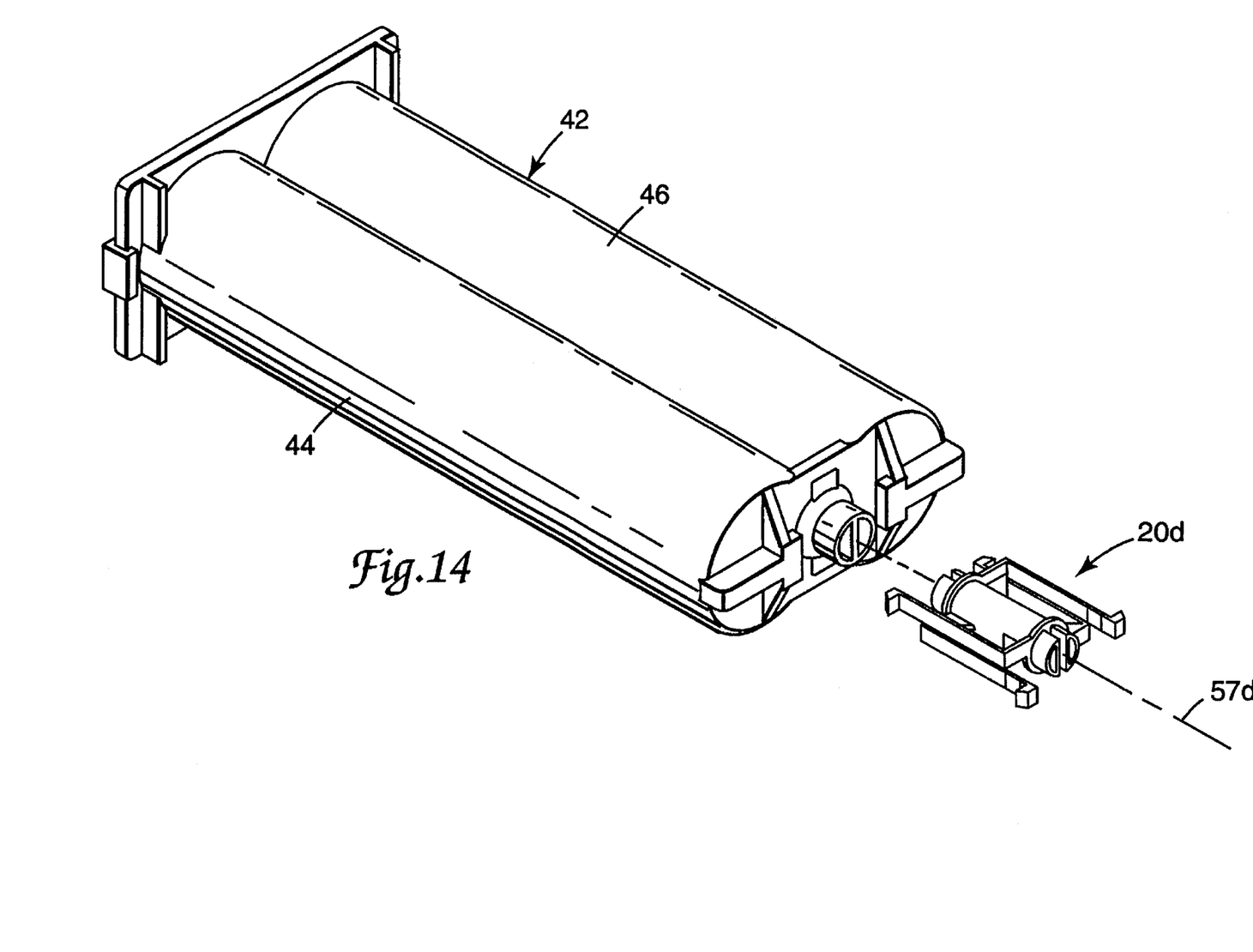
FIG. 14 is a reduced perspective view of the refilling device shown in FIGS. 12 and 13 along with a portion of a dual chamber dispensing cartridge, as the device and cartridge might appear before they are coupled together.
Figure 15:
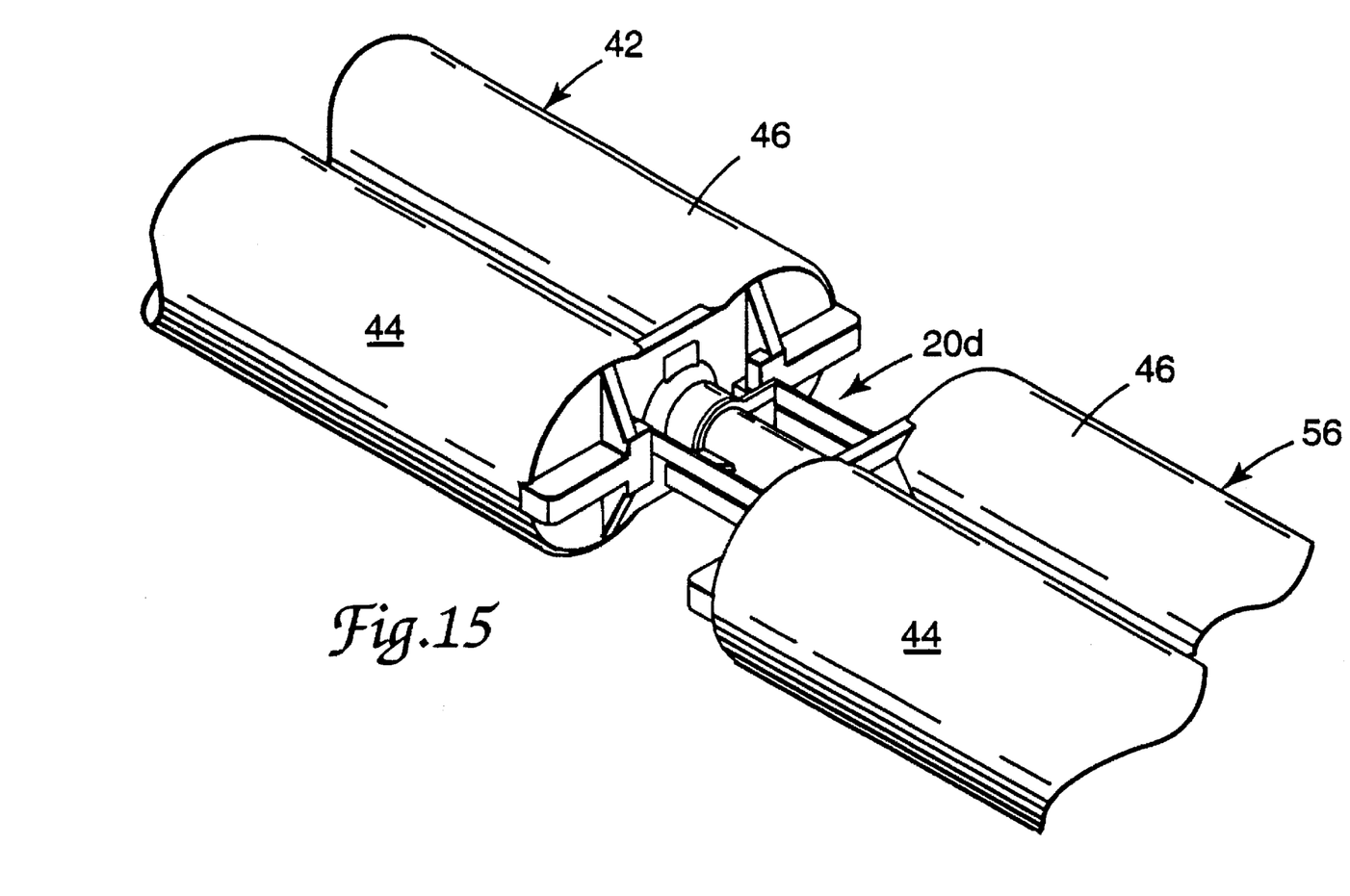
FIG. 15 is a fragmentary, reduced perspective view somewhat similar to FIG. 14 except that a second dual chamber dispensing cartridge has been added and the refilling device has been illustrated as coupling the two cartridges together.

In use, the device 20d is oriented relative to the dispensing cartridge 42 in the manner shown in FIG. 14 such that the projections 27d are aligned with the outlets 48, 50. As the device 20d is moved toward the cartridge 42 along reference axis 57d, the chamfered walls of the adjacent hooks 39d contact the tabs 52 and cause the legs 31d to deflect inwardly toward the body 22d until such time as the hooks 39d have moved past the tabs 52. As soon as the hooks 39d of the legs 31d have entered the space between the tabs 52 and the front end of the containers 44, 46 of the cartridge 42, the resilient legs 31d self-move in a direction away from the body 22d and return toward their normal configuration as is illustrated in FIG. 15. Preferably, the applicator is coupled to the cartridge 42 at this time and the plungers of the applicator are advanced to bleed air from the passages 24d, 26d. Next, a second cartridge 56 is connected to the device 20d by moving the second cartridge 56 in a similar manner until such time as the hooks 39d of the legs 33d have latched behind the tabs 52 of the second cartridge 56.

Preferably, the device 20d is integrally molded of a resilient material such as polypropylene. The distance between the hooks 39d of either coupler 30d, 32d and the adjacent plate 25d is selected so that such plate 25d is snugly compressed in flat, sealing engagement against the outer wall of the protruding outlet conduit 51 including the baffle. After the components have been transferred from one cartridge to the other, the device 20d is released from the cartridges 42, 56 by pressing the legs 31d, 33d inwardly toward the body 22d until the hooks 39d have cleared the tabs 52 and then moving the device 20d away from the cartridges 42, 56 along axis 57d.

Preferably, the device 20d includes one or more orienting sections for orienting the device 20d to the cartridges 42, 56 to insure that only the first containers 44 are connected with the first passage 24d and only the second containers 46 are connected to the passage 26d. Although not shown, such orienting sections could be provided by making the shape of the first outlets 48 different than the shape of the second outlets 50, and by providing projections 27d that matingly fit only into the first outlets 48 or projections 29d that matingly fit only into the second outlet 50. Other orienting sections such as outwardly protruding orienting sections like the ones described in U.S. Pat. No. 4,974,756 may alternatively be employed.

If desired, a separate, soft, elastomeric gasket may be provided adjacent each plate 25d surrounding the projections 27d, 29d. The gasket facilitates sealing of the device 20d to the cartridges 42, 56 and enables the body 22d to be made of a stiffer material to improve its strength.

Optionally, the pistons of the cartridges 42, 56 are modified to reduce the likelihood of turning the pistons over as a selected host cartridge is refilled. Such modification may include lengthening of the pistons, or adding spaced apart legs to the piston to hinder such turning motion as may be desired in cartridges where the pistons have a disk-like shape of relatively small thickness.

Those skilled in the art may recognize that a variety of modifications, additions or alterations may be made to the currently preferred embodiments described in detail above without departing from the spirit of our invention. For example, the retainers and adapters may have other configurations to match other types of dispensing cartridges. Additionally, the coupling structure used to couple the cartridges 42, 56 to the refilling device may be constructed other than that which is shown by latching to other elements of the cartridges, or by using a housing that encloses both cartridges as well as the refilling device. As another alternative, the couplers may be provided as part of the cartridges and also used for connection to static mixers, so that a separate part that includes couplers such as a retainer (e.g., retainer 21a) would be unnecessary and only the body with the two passageways need be installed in the cartridge outlets before coupling the cartridges together. A number of other variations are also possible. Accordingly, the scope of the invention should not be deemed limited to the structure described above in detail, but instead only by a fair reading of the claims which follow along with their equivalents.

We claim:

1. A device for consolidating compositions contained in partially filled dual chamber dispensing cartridges comprising:

a body having a pair of side-by-side passages;

a first coupler for releasably coupling said body to a first dual chamber dispensing cartridge in an orientation wherein said passages are in communication with side-by-side outlets of the first cartridge; and a second coupler for releasably coupling said body to a second dual chamber dispensing cartridge in an orientation wherein said passages are in communication with side-by-side outlets of the second cartridge, said body also including at least two sealing sections for sealing contact with the first cartridge and the second cartridge when the first cartridge and the second cartridge are coupled by said first coupler and said second coupler to said body.

2. The device of claim 1, wherein said body has a generally cylindrical shape, and wherein said first coupler and said second coupler include flanges for releasable connection to the first cartridge and the second cartridge respectively.

3. The device of claim 2, wherein said device includes a hollow cylindrical member connected to said first coupler and said second coupler, and wherein said body is received in said cylindrical member.

4. The device of claim 3, wherein said body is rotatably connected to said cylindrical member.

5. The device of claim 3, wherein said device includes structure for retaining said body in said member.

6. The device of claim 5, wherein said body is non-releasably retained in said member.

7. The device of claim 3, wherein said member is integrally connected to said flanges of said first coupler and said second coupler.

8. The device of claim 2 including at least one outwardly extending arm for facilitating rotation of said member relative to one of the first cartridge and the second cartridge.

9. The device of claim 1, wherein said first coupler and said second coupler include outwardly extending, flexible legs for releasable connection to the first cartridge and the second cartridge respectively.

10. The device of claim 9, wherein each of said legs includes a hook.

11. The device of claim 1, wherein said first coupler and said second coupler include a generally U-shaped retainer with at least two pairs of outwardly extending flanges.

12. The device of claim 1 including an orienting section for preventing one of said passages from being placed in communication with a certain one of the outlets of the first cartridge and the second cartridge.

13. The device of claim 1, wherein said body, said first coupler and said second coupler are integrally molded of a plastic material.

14. The device of claim 1, wherein said body has a generally hollow interior with a dividing wall presenting said side-by-side passages.

15. The device of claim 14, wherein said first coupler and said second coupler include flanges for releasable connection to the first cartridge and the second cartridge respectively.

* * * * *